United States Patent
Bardach et al.

(10) Patent No.: US 8,900,614 B2
(45) Date of Patent: Dec. 2, 2014

(54) INTRA-ORAL DEVICE FOR TREATING OBESITY

(75) Inventors: Laura Bardach, Boonton, NJ (US); James Geduldig, Boonton, NJ (US); Salvatore Napoli, Florham Park, NJ (US)

(73) Assignee: Dynamic Mouth Devices, L.L.C., Boonton, NJ (US)

( * ) Notice: Subject to any disclaimer, the term of this patent is extended or adjusted under 35 U.S.C. 154(b) by 200 days.

(21) Appl. No.: 12/575,808

(22) Filed: Oct. 8, 2009

(65) Prior Publication Data

US 2010/0034860 A1 Feb. 11, 2010

Related U.S. Application Data

(62) Division of application No. 11/212,220, filed on Aug. 26, 2005, now abandoned.

(51) Int. Cl.
- *A61K 9/00* (2006.01)
- *A61P 3/04* (2006.01)
- *A61F 5/00* (2006.01)
- *A61F 5/56* (2006.01)

(52) U.S. Cl.
CPC ............... *A61F 5/0006* (2013.01); *A61F 5/566* (2013.01)
USPC .......................................................... 424/422

(58) Field of Classification Search
CPC ..................................................... A61F 5/0006
USPC .......................................................... 424/422
See application file for complete search history.

(56) References Cited

U.S. PATENT DOCUMENTS

| | | | |
|---|---|---|---|
| 2,288,470 A | 6/1942 | Lorraine | |
| 3,223,085 A | 12/1965 | Gores et al. | |
| 3,224,442 A | 12/1965 | Stubbs | |
| 3,416,527 A | 12/1968 | Hoef | |
| 3,503,127 A | 3/1970 | Kasdin et al. | |
| 3,505,995 A | 4/1970 | Greenberg | |
| 3,532,091 A | 10/1970 | Lerman | |
| 3,587,590 A | 6/1971 | Hastings | |
| 3,600,807 A | 8/1971 | Sipos | |
| 3,818,906 A | 6/1974 | Stubbs | |
| 3,996,934 A | 12/1976 | Zaffaroni | |

(Continued)

FOREIGN PATENT DOCUMENTS

AU 633269 B2 1/1993

OTHER PUBLICATIONS

U.S. Appl. No. 10/138,821.
U.S. Appl. No. 11/212,220.

(Continued)

*Primary Examiner* — Rachael E Bredefeld
(74) *Attorney, Agent, or Firm* — Lerner, David, Littenberg, Krumholz & Mentlik, LLP

(57) ABSTRACT

The present invention relates to an intra-oral device including a carrier that has an outside wall, an inside wall and an occlusal wall connecting the outside wall to the inside wall. The carrier has at least one inset and at least one insert carrying a beneficial agent that is adapted to fit the inset, and the beneficial agent is capable of promoting weight loss. The intra-oral device is positioned in a user's mouth so that the intra-oral device is in contact with the user's cheeks, lips and/or tongue and the beneficial agent passes through the mucosal membrane of the user's mouth.

23 Claims, 3 Drawing Sheets

(56) References Cited

U.S. PATENT DOCUMENTS

| | | | |
|---|---|---|---|
| 4,044,762 A | 8/1977 | Jacobs | |
| 4,327,725 A | 5/1982 | Cortese et al. | |
| 4,348,381 A | 9/1982 | Gaffar et al. | |
| 4,350,154 A | 9/1982 | Feldbau | |
| 4,554,154 A | 11/1985 | White | |
| 4,569,342 A | 2/1986 | von Nostitz et al. | |
| 4,765,324 A | 8/1988 | Lake, Jr. | |
| 4,920,984 A | 5/1990 | Furumichi et al. | |
| 4,935,225 A * | 6/1990 | Curtis et al. | 424/49 |
| 4,944,947 A | 7/1990 | Newman | |
| 5,015,628 A | 5/1991 | Reynolds | |
| 5,021,053 A | 6/1991 | Barclay et al. | |
| 5,052,410 A | 10/1991 | Stubbs | |
| 5,071,657 A | 12/1991 | Oloff et al. | |
| 5,082,007 A | 1/1992 | Adell | |
| 5,085,585 A | 2/1992 | Zimble | |
| 5,152,301 A | 10/1992 | Kittelsen et al. | |
| 5,194,003 A | 3/1993 | Garay et al. | |
| 5,200,194 A | 4/1993 | Edgren et al. | |
| 5,252,692 A | 10/1993 | Lovy et al. | |
| 5,286,490 A | 2/1994 | Grodberg | |
| 5,323,787 A | 6/1994 | Pratt | |
| 5,339,832 A | 8/1994 | Kittelsen et al. | |
| 5,346,935 A | 9/1994 | Suzuki et al. | |
| 5,365,624 A | 11/1994 | Berns | |
| 5,395,392 A | 3/1995 | Suhonen | |
| 5,460,527 A | 10/1995 | Kittelsen | |
| 5,562,895 A | 10/1996 | Tung | |
| 5,566,684 A | 10/1996 | Wagner | |
| 5,620,011 A | 4/1997 | Flowers | |
| 5,819,744 A | 10/1998 | Stoyka, Jr. | |
| 5,826,581 A | 10/1998 | Yoshida | |
| 5,834,427 A | 11/1998 | Han et al. | |
| 5,842,860 A | 12/1998 | Funt | |
| 5,895,641 A | 4/1999 | Usen et al. | |
| 5,924,422 A | 7/1999 | Gustafson | |
| 5,925,372 A | 7/1999 | Berner et al. | |
| 5,979,449 A | 11/1999 | Steer | |
| 5,980,249 A | 11/1999 | Fontenot | |
| 5,981,475 A | 11/1999 | Reynolds | |
| 5,993,413 A | 11/1999 | Aaltonen et al. | |
| 6,012,919 A | 1/2000 | Cross, III et al. | |
| 6,036,487 A | 3/2000 | Westerman | |
| 6,036,944 A | 3/2000 | Winston et al. | |
| 6,068,475 A | 5/2000 | Stoyka, Jr. | |
| 6,082,363 A | 7/2000 | Washburn | |
| 6,126,678 A | 10/2000 | Aaltonen et al. | |
| 6,210,699 B1 | 4/2001 | Acharya et al. | |
| 6,244,269 B1 | 6/2001 | Tyler | |
| 6,269,816 B1 | 8/2001 | Rigonatti et al. | |
| 6,321,752 B1 | 11/2001 | Spottiswoode et al. | |
| 6,412,489 B1 | 7/2002 | Sue | |
| 6,494,210 B1 | 12/2002 | Mams | |
| 6,505,626 B2 | 1/2003 | Kittelsen et al. | |
| 6,514,176 B1 | 2/2003 | Norton | |
| 6,519,781 B1 | 2/2003 | Berns | |
| 6,553,996 B2 | 4/2003 | Kittelsen et al. | |
| 6,581,604 B2 | 6/2003 | Cook | |
| 6,592,860 B1 * | 7/2003 | Levy et al. | 424/78.08 |
| 6,635,281 B2 | 10/2003 | Wong et al. | |
| 6,660,029 B2 | 12/2003 | VanSkiver et al. | |
| 6,675,806 B2 | 1/2004 | Kittelsen et al. | |
| 6,691,710 B2 | 2/2004 | Kittelsen et al. | |
| 7,118,376 B2 | 10/2006 | Jodaikin et al. | |
| 7,328,706 B2 | 2/2008 | Bardach et al. | |
| 8,181,655 B2 | 5/2012 | Bardach et al. | |
| 8,505,541 B2 | 8/2013 | Bardach et al. | |
| 2003/0205234 A1 | 11/2003 | Bardach et al. | |
| 2005/0175959 A1 | 8/2005 | Jodaikin et al. | |
| 2006/0185679 A1 | 8/2006 | Costigan et al. | |

OTHER PUBLICATIONS

U.S. Appl. No. 11/250,210.
U.S. Appl. No. 11/891,649.
U.S. Appl. No. 12/001,571.
U.S. Appl. No. 12/228,584.
U.S. Appl. No. 12/229,444.

* cited by examiner

INTRA-ORAL DEVICE FOR TREATING OBESITY

CROSS-REFERENCE TO RELATED APPLICATION

This application is a divisional application of U.S. patent application Ser. No. 11/212,220, filed on Aug. 26, 2005, the disclosure of which is hereby incorporated herein by reference.

FIELD OF THE INVENTION

The present invention relates to a method and apparatus for treating obese or overweight patients including an intra-oral device that is worn on an arch of teeth that is adapted to deliver a beneficial agent and participate in the modulation of eating behavior.

BACKGROUND OF THE INVENTION

There is a growing concern about weight management in the United States and worldwide. The adverse health risks of overweightness and obesity are well known and include increased risk of coronary heart disease, cancer, stroke, high blood pressure, gallbladder and liver disease, osteoarthritis, gout, Metabolic Syndrome and diabetes.

Metabolic Syndrome is a major public health crisis, globally. It is characterized by a group of metabolic risk factors in one person, including: central obesity (excessive fat tissue in and around the abdomen); atherogenic dyslipidemia (blood fat disorders that foster plaque buildups in artery walls); raised blood pressure; insulin resistance or glucose intolerance; prothrombotic state; and proinflammatory state. The underlying causes of this syndrome are overweightness and obesity, physical inactivity and genetic factors. People with the metabolic syndrome are at increased risk of coronary heart disease, other diseases related to plaque buildups in artery walls like stroke and peripheral vascular disease, and type 2 diabetes.

Despite the fact that these health risks are well known, being overweight and obesity are prevalent in the United States. It is estimated that over 60% of American adults are overweight, meaning weighing more than is normal or necessary, especially having more body weight than is considered healthy for one's age, height, sex or build, or having a body mass index (BMI) of 25 to 29.9. Even more alarming, over 25% of American adults are obese. Obesity is defined as having a BMI of 30 or higher. BMI is a mathematical formula based on a person's height and weight. BMI is widely used by health care providers in determining whether a person is overweight or obese because it is closely associated with the measure of body fat, and may predict the development of health problems related to excess weight.

Generally, weight gain occurs when a person consumes more calories that he or she burns. Genetic, environmental, sociological and psychological factors contribute to weight gain, and consequently, overweightness or obesity. Several studies have shown that heredity is linked to obesity. Environmental and sociological factors also influence weight management inasmuch as lifestyle behaviors such as what a person eats and his or her level of physical activity directly influence the amount of calories consumed and burned.

Psychological factors have a significant affect on eating habits. Many people eat in response to negative emotions such as boredom, sadness, loneliness, depression, anxiety, anger and stress. This is referred to as "emotional eating." Many of these people eat, even when they are not physiologically hungry at all. Weight gain is a natural consequence of this overeating.

Overeating is a significant cause of overweightness. It is believed that there are three interconnected neurological anatomic nexuses that regulate food intake. The nexuses are the hunger center, which is located in the hypothalamus section of the brain, the appetite center, located in the brain stem, and the satiety center, which is connected to the hunger center and the appetite center. This feedback complex is further modulated by adipose tissue, endocrine organs and other humoral factors.

The hunger center is involved in the long term, metabolic regulation of food intake over weeks and months, and controls physiological hunger. When the human body actually requires nutrients, it will manifest this need with hunger or the stomach sensations we all identify as hunger.

Appetite, or the desire or inclination to eat, involves the short-term, environmental regulation of feeding from hour to hour over the course of a day. Appetite, as opposed to hunger, is a learned response to food and can be triggered by sensory cues at times when hunger is not present and eating is not required. Appetite may also be influenced by the psychological appeal of certain "eating behaviors" such as salivating, visualizing, smelling, tasting, chewing and swallowing food. When these eating behaviors have been satisfied, the desire to eat is abated. Many individuals eat when they are not hungry to satisfy their appetite.

It is extremely difficult for many people to lose weight of their own accord. Because one of the factors contributing to overweightness or obesity is psychological, medical treatment alone is often ineffective. Dieting can be successful in the short term, however, dieting is not effective for maintaining a desired weight long term. Most people who lose weight by dieting regain the weight they have lost, plus about ten extra pounds within five years. Behavior modification, i.e. changing habits relating to emotional eating, addresses the psychological factors that influence overeating and weight gain. There is a need for a successful method of promoting weight loss and weight management that provides an alternative to those who are compelled to eat when they are not hungry by providing the sensations necessary to satiate the appetite without the ill effects of excess calorie consumption.

A common method of treatment directed towards appetite suppression is administration of an appetite suppressant, in pill form. The drawbacks of this method of appetite suppression include peaks and troughs in the blood level of the active ingredient because the active ingredient is often not within a therapeutic range, psychological aversion to swallowing pills and user compliance where the pills must be taken at specific times. Another potential method of treatment directed towards appetite suppression is the intravenous, intramuscular or subcutaneous administration of agents that cannot be given enterically. The major drawback of this method of appetite suppression is the impracticality of self-administration. Another potential method of treatment directed towards appetite suppression is surgical alteration of various components of the gastrointestinal tract such as placation, stapling, bypass and other operations on the stomach and small intestines. The major drawback of surgical alteration techniques is a high degree of morbidity, this it is almost always reserved as a treatment of last resort. Therefore, an alternative method of administering an appetite suppressant is needed.

Accordingly, the present invention contemplates new and improved methods of reducing weight and diminishing appetite that overcome the above-referenced problems and others.

SUMMARY OF THE INVENTION

The present invention provides an intra-oral device including a carrier that has an outside wall, an inside wall and an occlusal wall connecting the outside wall to the inside wall. The carrier has at least one inset and at least one insert carrying a beneficial agent that is adapted to fit the inset, and the beneficial agent is capable of promoting weight loss. In a preferred embodiment, the insert is a hydrogel. In another preferred embodiment, the beneficial agent has time release properties. The intra-oral device is positioned in a user's mouth so that the intra-oral device is in contact with the user's cheeks, lips and/or tongue and the beneficial agent passes through the mucosal membrane of the user's mouth. The inset can be in the outside wall or the inside wall of the intra-oral device.

In one embodiment of the present invention, the beneficial agent is delivered systemically to the user. In another embodiment of the present invention, the beneficial agent is delivered to the user locally.

The beneficial agent of the present invention includes, but is not limited to, appetite suppressants, agents that provide a gustatory or aromatic stimulant, agents that are capable of decreasing good absorption, agents that are adapted to cause a physical change in the body that is expected to result in weight loss and agents that are adapted to cause a change in the behavior of a user that is expected to result in weight loss.

In another embodiment of the present invention, an intra-oral device is provided that does not cover the front teeth of a user. In yet another embodiment of the present invention, an intra-oral device is provided that has perforations in the carrier so that the beneficial agent can pass through the perforations when the beneficial agent is discharged from the insert. In a preferred embodiment of the invention, the intra-oral device has a wing extending from the inside wall of the carrier of the intra-oral device, and the wing has an inset that receives an insert carrying a beneficial agent.

The present invention also provides a method for treating weight loss and weight management in humans by positioning an intra-oral device having a carrier that has at least one inset and at least one insert adapted to fit into the inset in the mouth so that the insert is in contact with the mucosal membrane of the human's mouth, and the insert carries a beneficial agent that is capable of promoting weight loss. In a preferred embodiment, the insert is a hydrogel. In another preferred embodiment the beneficial agent has time release properties.

BRIEF DESCRIPTION OF THE DRAWINGS

The above brief description as well as other objects, features and advantages of the present invention will be more fully appreciated by reference to the following detailed description of the presently preferred but nonetheless illustrative embodiments in accordance with the present invention when taken in conjunction with the accompanying drawings, wherein.

DETAILED DESCRIPTION

Figure 1:
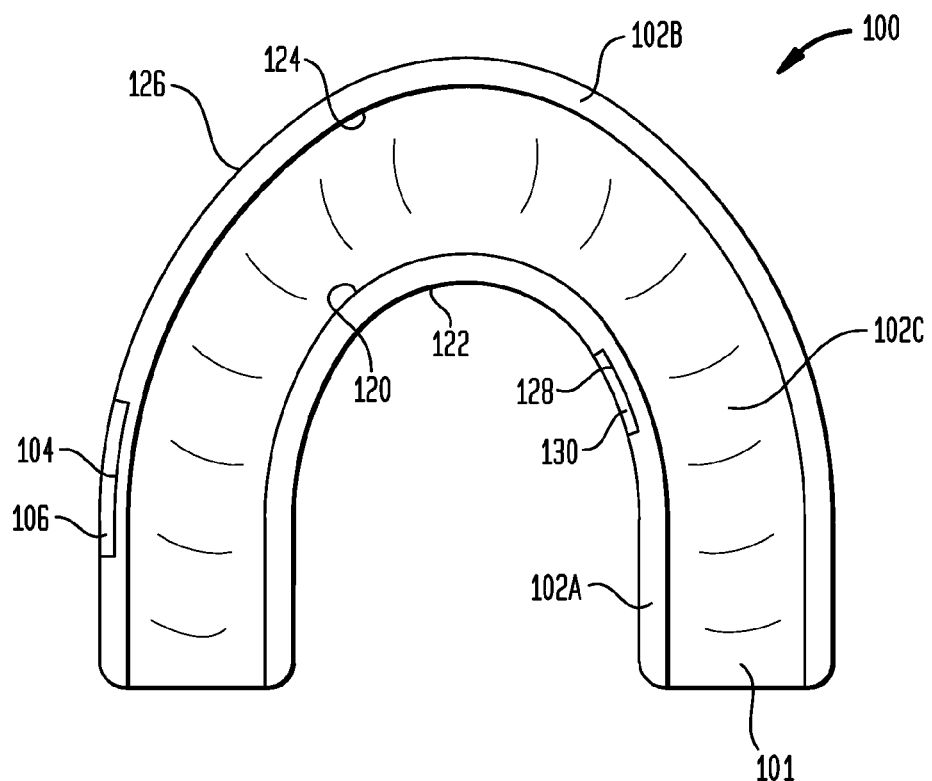
FIG. 1 is a top plane view of an intra-oral device showing the open channel of a U-shaped carrier.
Figure 2:
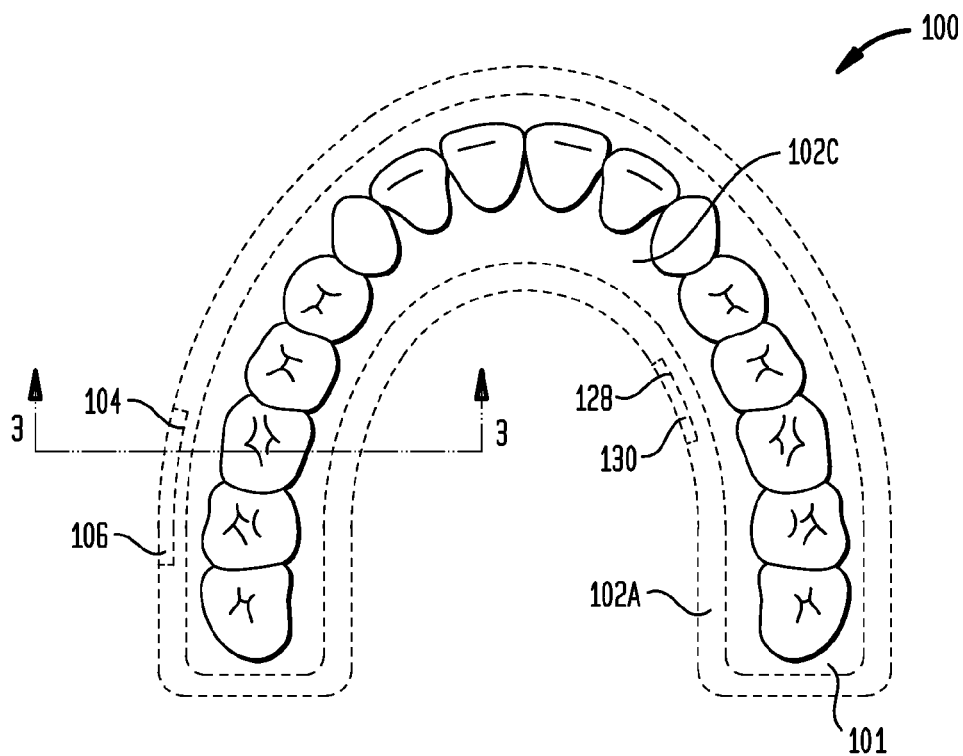
FIG. 2 is a top plane view of an intra-oral device being shown in phantom on the teeth of the upper or lower jaw.

Referring to FIGS. 1 and 2, an intra-oral device is shown as a U-shaped carrier 100. A device of a same type is disclosed in Applicants' co-pending application, Publication No. 20030205234, the disclosure of which is hereby incorporated by reference. Carrier 100 has a channel 101 serving as a recess for receiving an arch of teeth. Carrier 100 can be positioned over the user's upper teeth or the user's lower teeth. If the device is worn on the upper teeth, it may be referred to as a maxillary device. If the device is worn on the lower teeth, it may be referred to as a mandibular device.

Channel 101 is formed by an inside wall 102A, an outside wall 102B and an occlusal wall 102C. The inside wall 102A is referred to as the lingual/palatal wall. The inside wall 102A has an inner surface 120 and an outer surface 122. In a maxillary device, the inner surface 120 of the inside wall 102A touches the user's teeth, gingiva and palate, and the outer surface of the inside wall 102A may touch the upper (dorsal) surface of the user's tongue. In a mandibular device, the inner surface 120 of the inside wall 102A touches the teeth, gingival and lingual surface of the dentoalveolar process, and the outer surface 122 of the inside wall 102A will touch the undersurface (ventral) of the tongue. The outside wall 102B is referred to as the buccal/labial wall. The outside wall 102B has an inner surface 124 and an outer surface 126. In a maxillary and mandibular device, the inner surface 124 of the outside wall 102B touches the user's gingival and teeth and the outer surface 126 of the outside wall 102B touches the user's cheeks and lips. The occlusal surface 102C connects the inside wall 102A to the outside wall 102B. Surfaces 102A, 102B and 102C are collectively referred to as walls 102.

In this embodiment, the device has only a single channel for receiving the arch of teeth, but other embodiments may have two channels for receiving an arch of teeth from the upper jaw and an arch of teeth from the lower jaw. In the embodiment with two channels, the device has a clam-shape, with the occlusal surfaces of each channel facing each other. In use, one channel will face the user's nose for receiving the teeth from the upper jaw, and the other channel will face the user's chin for receiving the teeth from the lower jaw.

The intended material for carrier 100 may, for various embodiments, be any such material as is currently used in therapeutic intra-oral carriers or sports mouthguards. Mouthguards are typically made from plastic materials such as an ethylene vinyl acetate copolymer (EVA). Additives may be added to the EVA itself to provide special chemical or physical properties for different application. In some embodiments of this device, flavoring and aromatic agents may be added to the polymer. Colorants, perfumes and softening agents may be added as well. For example, German patent 4011204 discloses a mouthguard material consisting of an EVA copolymer material, polycaprolactone, colorants, perfumes and polyvinyl acetate (PVA). The softening point of the resultant mouthguard is reduced for ease of manipulation and shaping.

Carrier 100 has one or more insets arranged to maximize effective administration of a beneficial agent. The insets may be placed on the inner or outer surfaces of the walls 102 of the maxillary or mandibular carrier 100. Inset 104 is a recess in the outer surface 126 of outside wall 102B. Inset 128 is a recess in the outer surface 122 of inside wall 102A.

Each inset 104, 128 is adapted to receive an insert 106, 130. The walls of the insets are undercut to provide for a mechanical "snap-in" of the insert 106, 130. In a plane perpendicular to the surface of any of walls 102, the upper and lower surfaces of insert 106, 130 and inset 104, 128 are, in part, divergent in the direction towards the central channel in order to accomplish this snap-in, or locking, feature. The surfaces of the inset and insert may join at a bevel, rounded edge, obtuse, right or acute angle, or any other configuration that achieves the snap-in feature. For example, FIG. 3, which shows a cross sectional view of the device of FIG. 2, taken along the line 3-3, shows insert 106 having a beveled edge 108 to accomplish this snap-in feature.

Figure 4:
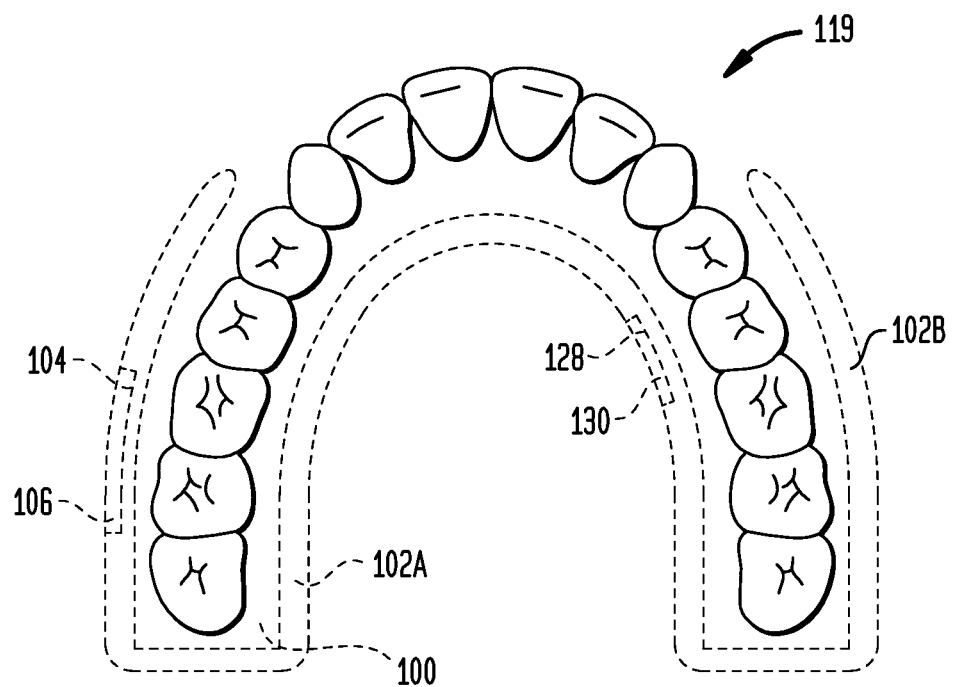
FIG. 4 shows a top plane view of an intra-oral device that does not cover the front teeth being shown in phantom on the teeth of the upper or lower jaw.

FIG. 4 shows yet another embodiment of the present invention. FIG. 4 shows an intra-oral device with a U-shaped carrier 100 where the outside wall 102B of the carrier does not extend to cover the front teeth, for inconspicuous wear. There is a gap 119 in the outside wall of the U-shaped carrier of the intra-oral device. Typically, the gap 119 will be big enough so that the user's canines and incisors are visible, however, the size of the gap can vary. The inside wall 102A of the intra-oral device is continuous so that the U-shape of the intra-oral device is maintained. In an intra-oral device where the outside wall does not cover the front teeth, there may be a wing 116 extending from the inside wall of the intra-oral device, at any position of the intra-oral device, just like in an intra-oral device where the outside wall is continuous.

Figure 5:
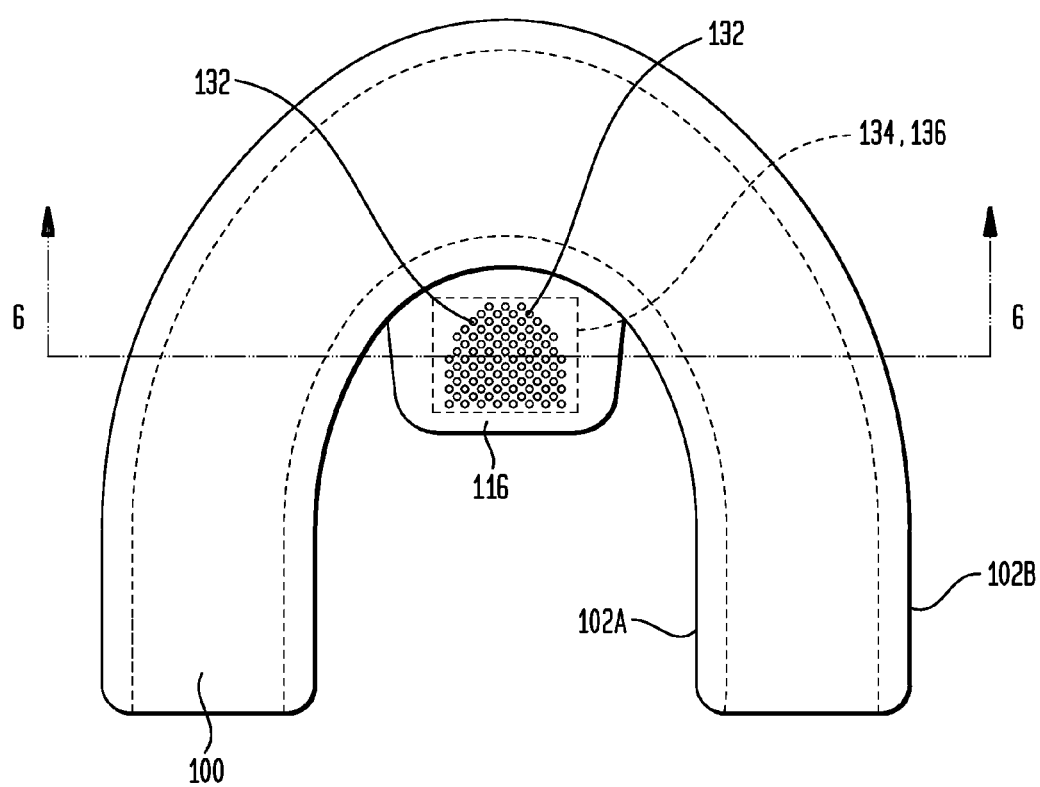
FIG. 5 is a bottom plane view of an intra-oral device showing a wing with perforations.
Figure 6:
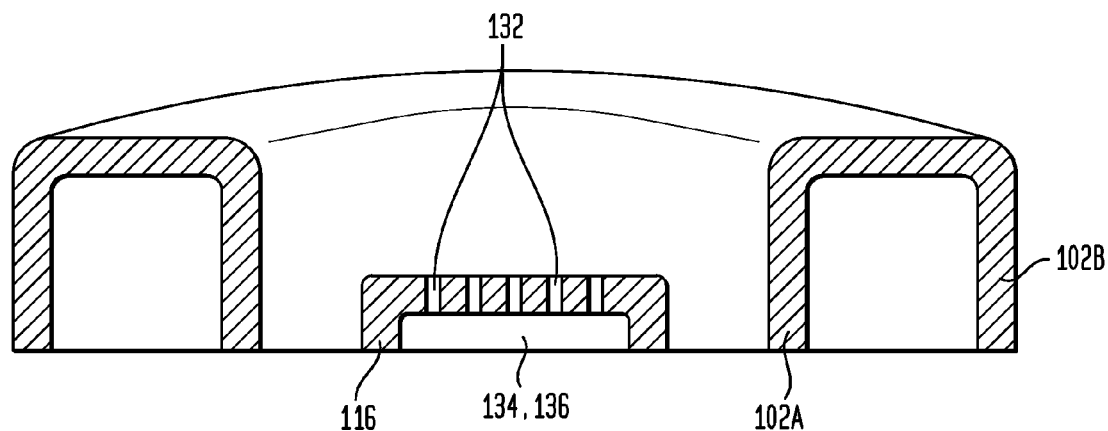
FIG. 6 is a detailed, cross sectional view of the intra-oral device of FIG. 5 taken along the line 6-6.

Referring to FIGS. 5 and 6, another embodiment of the present invention is shown. FIG. 5 shows an intra-oral device with a U-shaped carrier 100 of the type as previously described and a generally flat wing 116 extending from the inside wall 102A of the intra-oral device. In a maxillary device, the inner surface of the wing 116 touches the roof of the user's mouth and the outer surface of the wing touches the top of the user's tongue. In a mandibular device, the inner surface of the wing touches the floor of the user's mouth, and the outer surface of the wing touches the bottom of the user's tongue. The wing may be located at any position of the intra-oral device about the carrier. The wing may also extend from anywhere on the inside wall from the top to the bottom of the device. In either embodiment, the inset 134 (shown in phantom) and insert 136 (shown in phantom) are located on one surface of the wing and the perforations 132 are located on the opposite surface of the wing. The perforations 132 extend into the wing into communication with the insert 136. FIG. 5 is a mandibular device and shows perforation(s) 132 on the outer surface of wing 116. The perforations allow the user to apply pressure to the surface of the intra-oral device with the tongue and cause an increase, or a surge release, of the beneficial agent contained in the insert through the perforations. FIG. 6 shows a cross sectional view of the device of FIG. 5, taken along the line 6-6.

One or more insets can be located at any position on the surfaces of the walls 102. The insets can be located on the outer or inner surfaces of walls 102A or 102B. By way of example, in a maxillary or mandibular device, a pair of insets 104 may be located opposite each other on the outermost surface of the outside wall, each laterally adjacent to the molar and premolar teeth 106.

The inset is capable of receiving an insert carrying a beneficial agent. Blank inserts that do not carry a beneficial agent may also be adapted to fit the insets to maintain the shape and integrity of the insets. In an embodiment wherein there are multiple insets, a combination of blank inserts and inserts carrying a beneficial agent may be utilized.

For transbuccal administration, as explained further hereinafter, the insets will be located on the outermost surface of outside wall 102B of channel 101 so that contact is created between the buccal mucosa, i.e. the inner cheek and lips, and the device.

In one embodiment of the present invention, there is provided a method of promoting weight loss and weight management using the intra-oral device provided herein where the act of wearing the intra-oral device in the mouth satisfies oral fixation instead of the act of eating. In this embodiment, the use and placement of inserts into the insets is secondary. The intra-oral device can be inserted into the mouth whenever a person has the desire to eat because of an emotion or experiences hunger. The intra-oral device will be removed when the person determines that his or her desire to eat is extinguished.

In another embodiment of the present invention, the intra-oral device provides a tactile, gustatory and/or aromatic stimulant instead of or in addition to a drug delivery system. Tactile, gustatory and aromatic stimulants can act to suppress appetite. The eating factors can be satisfied when a person tastes or smells food, instead of eating, because the brain believes that the body has actually eaten. Thus, by providing a gustatory or aromatic stimulant in combination with the pseudo-masticatory, tactile stimulation of the intra-oral device, the appetite will be satisfied. Overeating will decrease, leading to weight loss and weight management.

The gustatory stimulation effect takes place when the device comes in contact with the oral cavity. The aromatic stimulation begins just prior to insertion of the device into the mouth as odor molecules enter through the nose into the nasal cavity, which houses the smell receptors. The aromatic stimulation continues while the device is in the mouth as airborne odor molecules are exhaled through the nasopharynx into the nasal cavity, or exhaled through the mouth and subsequently inhaled through the nose. Therefore, it is possible to administer an aromatic stimulant through the mouth.

The psychological appeal of a particular eating behavior, or the appetite satisfying property of chewing food, is sublimated by the user's ability to "bite" and "grind" into the intra-oral device. Thus, any non-hunger driven desire to "chew food" is sublimated into an activity that does not involve a significant caloric intake.

The intra-oral device is an object that, because of its aromatic, gustatory and tactile properties, deceives the brain into interpreting it as food, thereby stimulating salivation, which is the first part of the digestion of food. Thus, a user's specific eating behavior of generating saliva and swallowing is satisfied by insertion of the intra-oral device.

The intra-oral device in this embodiment is exposed to a solution containing a gustatory and/or aromatic stimulant before being inserted into the mouth. This exposure can be soaking the device in a solution containing a gustatory and/or aromatic stimulant until it is imbibed with the solution. When the gustatory and/or aromatic stimulant is used up, that is, it is not capable of providing a gustatory and/or aromatic effect, the intra-oral device can be replenished. This can be done by soaking the device in the solution again, and it can be done repeatedly.

In this embodiment, the inset(s) are fitted only with blank insert (s). The coated intra-oral device can be inserted into the mouth whenever a person has the desire to eat because of an emotion or experiences hunger. The intra-oral device will be removed when the person determines that his or her desire to eat is extinguished.

In other embodiments of the present invention, the insets are fitted with inserts capable of carrying a beneficial agent. The preferred insert will be composed of a material that will be able to contain and release a beneficial agent with certain properties at an effective rate and concentration. By beneficial agent, it is meant any substance capable of producing a desired effect. One desired effect in accordance with the present invention is reducing or extinguishing appetite.

Another desired effect in accordance with the present invention is a physical change in the body that results in weight management or weight loss. Yet another desired effect in accordance with the present invention is a change in the behavior of the user that results in weight management or weight loss.

A more preferred vehicle for delivery of the beneficial agent is an insert capable of releasing the agent over an extended period of time.

The preferred vehicle for agent delivery is a hydrogel, such as commercially available hydrogels. An example of such a hydrogel may be a hydrophilic acrylate derivative, with each polymer chain having several sequences of units with pendant hydrophilic groups, called soft blocks, and several sequences of pendant nitrile groups, called hard blocks. The lengths of the blocks, and/or the nature of the side groups, as well as the overall hydrophilicity of the polymer, are varied depending upon production conditions.

An advantage of using a hydrogel delivery system is that the hydrogel inserts act as a diffusion barrier that allows the agents to be released over a period of hours. It is contemplated that other hydrogels and agent-releasing inserts may be used in other embodiments of the present invention. For example, other hydrogels which are contemplated by the present invention include compounds such as polyhydroxy-ethyl methacrylate, chemically or physically crosslinked polyacrylaminde, polyvinyl alcohols, poly(N-vinyl pyrolidone), polyethylene oxide, and hydrolyzed polyacrylonitrile. Polysaccharide-based hydrogels, such as covalent or chemically crosslinked polyvalent metal salts of alginates, pectins, carboxymethylcellulose, heparin and hyaluronic acid, as well as hydrogels containing chitin, chitosan, gellan, pullulan and xanthan are also contemplated by the present invention.

In one embodiment of the present invention, the beneficial agent provides a gustatory and/or aromatic stimulant. The beneficial agent can include any combination of flavors and/or odors. The beneficial agent can also include vitamins, minerals, herbal supplements and/or other dietary constituents and substitutes. In this embodiment, the beneficial agent is delivered locally to evoke gustatory and/or aromatic stimulation of the brain. The stimulation of the brain produces the desired effect of reducing or extinguishing appetite and causing a change in the behavior of the user that results in weight management or weight loss because the tendency to overeat will diminish.

In another embodiment of the present invention, the beneficial agent is a drug. There are beneficial drugs that cannot be delivered enterically because they are inactivated by the gastrointestinal tract or their gastrointestinal absorption is not possible or inconsistent. It has been shown that there are several advantages of transmucosal administration of drugs. In general, drug delivery through the mucosal membrane prevents drugs from degradation in the gastrointestinal tract. When the hydrogel insert comes into contact with the oral mucosa, the beneficial agent is released from the hydrogel and passes through the mucosal membrane, and is absorbed directly into the circulatory system. The beneficial agent is delivered systemically to cause a physical effect in the body.

When the beneficial agent is released, it can be absorbed by any mucosal membrane in the mouth, and not just the buccal mucosal membrane.

The beneficial agent to be delivered systemically can be a drug or other substance that is capable of reducing or suppressing the appetite. Such drugs and substances include, but are not limited to: Cholecystokinin (CCK), Bombesin/Gastrin-Releasing Peptide (GRP), Enterostatin, Glucagon-like peptide 1 (GLP-1), neuropeptide-Y, Galanin, Orexin, cocaine- and amphetamine-regulated transcript (CART), Melanocortins, serotonin (5-HT), noradrenaline (NA), and leptin. These drugs and substances cause a physical change in the body.

The above mentioned agents have different properties that are effective in promoting weight loss. Appetite suppressant agents which act via peripheral satiety peptide systems include Cholecystokinin (CCK), Bombesin/Gastrin-Releasing Peptide (GRP), and Enterostatin, Glucagon-like peptide 1 (GLP-1). Appetite suppressant agents which alter the CNS levels of levels of various hypothalamic neuropeptides include neuropeptide-Y, Galanin, Orexin, cocaine- and amphetamine-regulated transcript (CART) and Melanocortins. Appetite suppressant agents which alter the levels of the key CNS appetite monoamine neurotransmitters include serotonin (5-HT) and noradrenaline (NA). The peptide hormone leptin has been regarded as a hormonal signal significant in fat tissue metabolism, and stimulates leptin and other related receptors. These receptors may also provide targets for other drugs that may be delivered by a transmucosal route.

In yet another embodiment of the present invention, the agent is capable of decreasing food absorption. For example, glucomannan, a water soluble dietary fiber extracted from the konjac root, is slowly digested by the body. It helps slow down the absorption of carbohydrates found in foods and also produce a feeling of fullness when ingested before a meal. Glucomannan is often found in powdered or in capsule form, however, it can be adapted for delivery through a hydrogel for use with the present invention.

It is further contemplated that a substance capable of absorbing dietary fat that is normally absorbed into the bloodstream may be included in the beneficial agent, such as chitosan. Other herbal agents that influence appetite and eating behavior such as guar gum, plantago husk, alfalfa, bladderwrack and ginger root can also be adapted for delivery through a hydrogel for use with the present invention.

Figure 3:
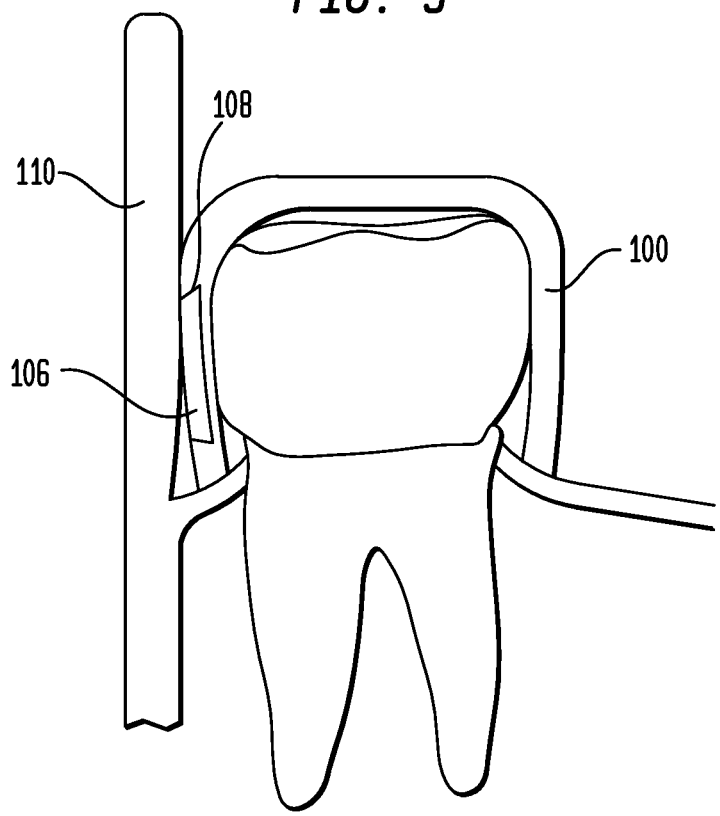
FIG. 3 is a detailed, cross sectional view of the intra-oral device of FIG. 2 taken along the line 3-3.

For systemic delivery of a drug or other substance, the beneficial agent is delivered through the oral mucosal membrane when contact is created between the hydrogel and the inner cheek and/or lips, or ventral surface of the tongue. Referring to FIG. 3, the carrier 100 is positioned on a user's lower teeth. The insert 106 is in contact with the user's cheek 110, which allows for passage of the beneficial agent through the buccal membrane. The hydrogel releases the beneficial agent over time and in appropriate quantities. The intra-oral device will be removed when an effective amount of the beneficial agent is delivered.

An effective amount of the beneficial agent is an amount sufficient to reduce or extinguish the appetite, cause a physical change in the body that results in weight management or weight loss, or cause a change in the behavior of the user that results in weight management or weight loss. Use over a period of time results in weight loss or weight management due to the decrease in amount of food consumed by the user.

In yet another embodiment of the present invention, the inner surface or the outer surface of the inside wall of a maxillary or mandibular device may be perforated at the location of the inset(s) as in the case of the wing 116. This will allow the user to apply pressure to the surface of the intra-oral device with the tongue and cause an increase, or a surge release, of the beneficial agent contained in the insert through the perforations. The beneficial agent is a chemical, therapeutic agent, medication, pharmaceutical, nutraceutical or any other substance capable of producing a desired effect, or any combination thereof. In another embodiment, the beneficial agent promotes weight loss or weight management.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of administering a beneficial agent to promote weight loss or weight management in humans comprising:
   instead of eating, positioning an intra-oral device over an arch of teeth of a user when said user has a desire to eat; wherein said intra-oral device includes a carrier having an outside wall, an inside wall, and an occlusal wall connecting said outside wall to said inside wall; and wherein said intra-oral device contains a beneficial agent for promoting weight loss or weight management selected from the group consisting of flavors, odors, appetite suppressants, agents for decreasing food absorption, agents for absorbing dietary fat, herbal compounds, chemicals, therapeutic agents, medications, pharmaceuticals, nutraceuticals and combinations thereof.

2. The method of claim 1, further comprising:
   removing said intra-oral device from said user's mouth when said beneficial agent extinguishes said user's desire to eat.

3. The method of claim 1, wherein said beneficial agent is flavors, odors, and a combination of flavors and odors.

4. The method of claim 3, further comprising exposing said intra-oral device to a solution comprising said beneficial agent before positioning said intra-oral device over said arch of teeth of said user.

5. The method of claim 4, wherein said step of exposing said intra-oral device to a solution comprises soaking said intra-oral device in said solution until said intra-oral device is imbibed with said solution.

6. The method of claim 3, further comprising replenishing said beneficial agent in said intra-oral device.

7. The method of claim 6, wherein said step of replenishing beneficial agent comprises soaking said intra-oral device in said solution until said intra-oral device is imbibed with said solution.

8. The method of claim 1, wherein said beneficial agent has time release properties.

9. The method of claim 1, wherein said carrier has at least one inset and at least one insert adapted to fit said inset, said insert carrying said beneficial agent.

10. The method of claim 1, wherein said beneficial agent is released by a delivery system comprising a hydrogel.

11. The method of claim 1, wherein said carrier includes at least one perforation.

12. The method of claim 11, further comprising applying pressure to said intra-oral device with said user's tongue to cause a discharge of said beneficial agent through said perforation.

13. The method of claim 1, wherein said beneficial agent is released by a delivery system comprising pullulan.

14. The method of claim 1, wherein said outside wall, said inside wall, and said occlusal wall of said carrier define at least one channel for embracing said arch of teeth; said carrier having a right-hand portion for embracing a portion of said arch of teeth on a right side of said user's mouth and a left-hand portion for embracing a portion of said arch of teeth on a left side of said user's mouth, and said carrier having an intermediate portion disposed between said right-hand portion and said left-hand portion and extending along at least a portion of said user's palate, wherein said intermediate portion carries said beneficial agent.

15. The method of claim 14, wherein said intermediate portion includes at least one inset and at least one insert adapted to fit said inset, said insert carrying said beneficial agent.

16. The method of claim 14, wherein said intermediate portion comprises a wing extending from said inside wall.

17. The method of claim 16, wherein said wing includes at least one inset and at least one insert adapted to fit said inset, said insert carrying said beneficial agent.

18. The method of claim 1, wherein said outside wall is provided with an opening adapted to expose at least one of said user's teeth.

19. A method of administering a beneficial agent to promote weight loss or weight management in humans comprising:
   positioning an intra-oral device over an arch of teeth of a user when said user has a desire to eat; wherein said intra-oral device includes a carrier having an outside wall, an inside wall, and an occlusal wall connecting said outside wall to said inside wall; wherein said outside wall is provided with an opening adapted to expose at least one of said user's teeth; and wherein said intra-oral device contains a beneficial agent for promoting weight loss or weight management selected from the group consisting of flavors, odors, appetite suppressants, agents for decreasing food absorption, agents for absorbing dietary fat, herbal compounds, chemicals, therapeutic agents, medications, pharmaceuticals, and nutraceuticals.

20. A method of administering a beneficial agent to promote weight loss or weight management in humans comprising:
   positioning an intra-oral device over an arch of teeth of a user when said user has a desire to eat; wherein said intra-oral device includes a carrier having an outside wall, an inside wall and an occlusal wall connecting said outside wall to said inside wall; wherein said intra-oral device contains a beneficial agent for promoting weight loss or weight management selected from the group consisting of flavors, odors, appetite suppressants, agents for decreasing food absorption, agents for absorbing dietary fat, herbal compounds, chemicals, therapeutic agents, medications, pharmaceuticals, and nutraceuticals; and wherein said outside wall, said inside wall, and said occlusal wall of said carrier define at least one channel for embracing said arch of teeth; said carrier having a right-hand portion for embracing a portion of said arch of teeth on a right side of said user's mouth and a left-hand portion for embracing a portion of said arch of teeth on a left side of said user's mouth, and said carrier having an intermediate portion disposed between said right-hand portion and said left-hand portion and extending along at least a portion of said user's palate, wherein said intermediate portion carries said beneficial agent.

21. The method of claim 20, wherein said intermediate portion includes at least one inset and at least one insert adapted to fit said inset, said insert carrying said beneficial agent.

22. The method of claim 20, wherein said intermediate portion comprises a wing extending from said inside wall.

23. The method of claim 22, wherein said wing includes at least one inset and at least one insert adapted to fit said inset, said insert carrying said beneficial agent.

* * * * *